United States Patent
Clark et al.

(10) Patent No.: US 6,946,140 B1
(45) Date of Patent: Sep. 20, 2005

(54) METHODS AND COMPOSITIONS FOR ENHANCING FIBROBLAST MIGRATION

(75) Inventors: Richard A. Clark, Poquott, NY (US); Dennis K. Galanakis, Stony Brook, NY (US); Azmin Kahn, Coram, NY (US)

(73) Assignee: The Research Foundation of State University of New York, Albany, NY (US)

( * ) Notice: Subject to any disclaimer, the term of this patent is extended or adjusted under 35 U.S.C. 154(b) by 0 days.

(21) Appl. No.: 09/500,512

(22) Filed: Feb. 9, 2000

Related U.S. Application Data

(60) Provisional application No. 60/119,344, filed on Feb. 9, 1999.

(51) Int. Cl.[7] .......................... A61F 13/00; C12N 5/00; C12Q 1/70
(52) U.S. Cl. .......................... 424/422; 435/325; 435/4; 435/29; 435/395
(58) Field of Search .............................. 435/325, 4, 29, 435/395; 424/422

(56) References Cited

U.S. PATENT DOCUMENTS

| | | | |
|---|---|---|---|
| 4,453,939 A | | 6/1984 | Zimmerman et al. |
| 4,627,879 A | | 12/1986 | Rose et al. |
| 4,950,483 A | | 8/1990 | Ksander et al. |
| 5,024,841 A | | 6/1991 | Chu et al. |
| 5,226,877 A | | 7/1993 | Epstein |
| 5,330,974 A | * | 7/1994 | Pines et al. |
| 5,643,192 A | | 7/1997 | Hirsh et al. |
| 5,935,850 A | * | 8/1999 | Clark et al. .................. 435/325 |

OTHER PUBLICATIONS

Gailit et al, Human fibroblasts bind directly to fibrinogen..., abstract, Exp. Cell Res. 1997, vol. 232(1), pp. 118-126.*
Gailit et al, Studies in vitro on the role of..., abstract, J. Invest. Dermatol. (1996), vol. 106(1), pp. 102-108.*
Brown et al., Fibroblast migration in Fibrin gel matrices, American Journal of Pathology, vol. 142, 142 No.1, Jan. 1993.*
Greiling et al., Fibronectin provides a conduit..., Journal of cell science, 1997, vol. 110, pp. 861-870.*
DeMoraes et al., Use of autologous fibrin glue in dermatologic surgery..., Sao Paulo Medical Journal, 1998, vol. 116(4), pp. 1747-1752.*
Gailit et al., Human fibroblast bind directly to fibrinogen..., Experimental cell research 1997, VOl. 232, pp. 118-126.*
Armani et al., BLOOD, 72(3):919-924 (1988).
Brennan, Blood Reviews, 5:240-244 (1991).
Clark et al., J. Investigative Dermatology, 79(5); 264-269 (1982).
Epstein et al. , Ann. Otol. Laryngol., 95:40-45(1986).
Farrugia, et al. TRANFUSION 32(8):755-759(1992).
Finnlayson et al., BIOCHEMISTRY, 2(1):42-46(1963).
Galanakis, Thrombosis Research, 78(4): 303-313(1995).
Greiling et al., J. Cell. Science, 110: 861-870(1997).
Harker et al., New England J. Med., 287(20):999-1005 (1972).
Kazal et al., P.S.E.M.B., 113:989-994(1963).
Masri et al., Thromb> Haemostas, 49:116-119(1983).
Mosesson et al., J. Clin. Investigation, 42(6):747-755(1963).
Mosesson et al., BIOCHEMISTRY, 5(9): 2829-2835(1966).
Siedentop et al., LARYGOSCOPE, 95:1074-1076(1985).
Staindi, Ann. Otol., 88:413-418(1979).
Stathakis et al., Thrombosis Research 13:467-475(1978).

* cited by examiner

*Primary Examiner*—Vickie Kim
(74) *Attorney, Agent, or Firm*—Rogalskyj & Weyand, LLP.

(57) ABSTRACT

Methods and compositions for enhancing fibroblast migration at a wound site are disclosed. The method includes contacting the wound site with fibrinogen that is prepared by a process which includes precipitating plasma with glycine. The compositions includes a lipid rich component and fibrinogen.

18 Claims, 4 Drawing Sheets

METHODS AND COMPOSITIONS FOR ENHANCING FIBROBLAST MIGRATION

The present invention claims priority of U.S. Provisional Patent Application No. 60/119,344, filed Feb. 9, 1999, which is hereby incorporated by reference.

The subject matter of this application was made with support from the United States Government under National Institutes of Health Grant No. AG 1101143-12. The United States Government may have certain rights in this subject matter.

FIELD OF THE INVENTION

The subject invention is directed to methods and compositions for enhancing fibroblast migration and promoting wound healing.

BACKGROUND OF THE INVENTION

Throughout this application various patents and publications are referenced, many in parenthesis. Full citations for each of the referenced publications are provided at the end of the Detailed Description. The disclosures of each of these patents and publications in their entireties are hereby incorporated by reference in this application.

It is estimated that in 1992, 35.2 million wounds required major therapeutic intervention in the US (Medical Data International, Inc. 1993). Surgical incisional wounds are performed with aseptic technique, and are closed by primary intention. Most repair and heal uneventfully. Many traumatic wounds and cancer extirpations, however, must be left open to heal by secondary intention. Furthermore, chronic wounds have significant tissue necrosis and fail to heal by secondary intention. It is estimated that 5.5 million people in the US have chronic, nonhealing wounds and that their prevalence is increasing secondary to the increase in age-related diseases, the increase in Acquired-immune Deficiency Syndrome ("AIDS"), and the increase of radiation wounds secondary to cancer intervention. In the US, approximately 1.5–2.5 million people have venous leg ulcers; 300,000–500,000 people have diabetic ulcers; and 2.5–3.5 million people have pressure ulcers (Callam et al. (1987); Phillips and Dover (1991); Lees and Lambert (1992); Lindholm et al. (1992)). These acute and chronic open wounds require long-term care and procedures that include skin grafting and tissue flaps, debridement, frequent dressing changes, and administration of pain medications. This care is costly and labor intensive. Furthermore, these wounds have a severe impact on the patients' quality of life. The chronic dermal ulcerations can cost as much as $40,000 each to heal, and more disappointing is that 50% reappear within 18 months of healing. Chronic dermal ulcers are also associated with mortality. As many as 21% of patients in intermediate-care facilities with pressure ulcers die (Bergstrom et al. (1994)).

Although multiple millions of dollars have been spent on the development of numerous recombinant growth factors (Abraham and Klagsbrun (1996); Heldin and Westermark (1996); Nanney and King (1996); Roberts and Sporn (1996)) and organotypic skin replacements (Boyce et al. (1995)) for use in open wounds over the past decade, the evidence of cost-effective benefit is meager thus far (Brown et al. (1989); Robson et al. (1992a); Robson et al. (1992b); Phillips et al. (1993)).

Many attempts have been made to produce a composition which can be used to facilitate wound repair.

Many of these compositions involve collagen as a component. U.S. Pat. Nos. 4,950,483 and 5,024,841 each discuss the usefulness of collagen implants as wound healing matrices. U.S. Pat. No. 4,453,939 discusses a wound healing composition of collagen with a fibrinogen component and a thrombin component, and optionally fibronectin. U.S. Pat. No. 4,970,298 discusses the usefulness of a biodegradable collagen matrix (of collagen, hyaluronic acid, and fibronectin) for wound healing. Yamada et al. (1995) disclose an allogeneic cultured dermal substitute that is prepared by plating fibroblasts onto a spongy collagen matrix and then culturing for 7 to 10 days. Devries et al. (1995) disclose a collagen/alpha-elastin hydrolysate matrix that can be seeded with a stromal-vascular-fraction of adipose tissue. Lamme et al. (1996) disclose a dermal matrix substitute of collagen coated with elastin hydrolysate. U.S. Pat. No. 5,489,304 and Ellis and Yannas (1996) each disclose a collagen-glycosaminoglycan matrix.

There are also numerous compositions which involve hyaluronic acid ("HA") as a component. Ortonne (1996), Borgognoni et al. (1996), and Nakamura et al. (1997) each discuss the usefulness of HA for wound healing. In Nakamura et al. (1997), HA was combined with chondroitin sulfate in one series of experiments. In U.S. Pat. No. 5,604,200, medical grade HA and tissue culture grade plasma fibronectin were used in combination with calcium, phosphate, uric acid, urea, sodium, potassium, chloride, and magnesium to create a moist healing environment that simulates the fetal in utero wound healing matrix. U.S. Pat. No. 5,631,011 discloses a composition of HA and fibrin or fibrinogen.

Various other compositions have also been explored for their wound healing capabilities. Kratz et al. (1997) used a gel of heparin ionically linked to chitosan. Bartold and Raben (1996) studied platelet-derived growth factor ("PDGF"). Henke et al. (1996) disclosed that chondroitin sulfate proteoglycan mediated cell migration on fibrinogen and invasion into a fibrin matrix, while Nakamura et al. (1997) concluded that chondroitin sulfate did not affect wound closure in a corneal epithelial wound. Henke et al. (1996) also disclosed that an anti-CD44 antibody blocked endothelial cell migration on fibrinogen. U.S. Pat. No. 5,641,483 discloses topical gel and cream formulations containing human plasma fibronectin for healing cutaneous wounds. Schultz et al. (1992) discloses a composition of epidermal growth factor ("EGF"), fibronectin, a synthetic collagenase inhibitor, and Aprotinin.

Fibrin matrices and components of fibrin matrices have been investigated for promoting wound healing. Besides being the ultimate plug of the hemostasis system, fibrin is part of a provisional matrix that provides tissue cells a scaffold for repopulation of a wound (Clark et al. (1982a)). Recently, however, it was discovered that fibroblasts, tissue mesenchymal cells, will not penetrate a pure fibrin clot (Greiling and Clark (1997)). Another plasma protein, fibronectin, normally found in blood clots must be present in the clot for fibroblast migration (Greiling and Clark (1997)).

Some fibrinogen preparations have been found to improve healing. Fibrin sealants, or glues, are topical, biologically compatible, resorbable tissue adhesive that initiate the last phases of coagulation during wound healing. The components of fibrin sealants typically consists of concentrated human fibrinogen in solution with various amounts of fibronectin and factor XIII, as well as other components. The fibrin sealants are activated by addition of thrombin and calcium chloride and subsequently form a coagulum (clot). Methods of obtaining the concentrated fibrinogen include precipitation of plasma by cryoprecipitation, polyethylene glycol or ammonium sulphate (Brennan (1991)). Contradictory results are obtained, however, for these preparations. In some instances, the fibrinogen preparations improve healing (Gelich et al. (1995); Saclarides et al. (1992), in others no improvement in healing was found (Lasa et al. (1993); Byrne et al. (1992). Further, animal studies have not been predicative of clinical use. In addition, the fibrin sealants utilized to date vary in purity levels.

In view of the severity of the problem of chronic, non-healing wounds, new and more effective matrices and methods for facilitating wound healing, and in particular, fibroblast migration are needed. The present invention is directed to meeting this need.

SUMMARY OF THE INVENTION

The present invention relates to a method for enhancing fibroblast migration at a wound site. The method includes contacting the wound site with fibrinogen that is prepared by a process which includes precipitating plasma with glycine.

Another aspect of the present invention relates to a method for enhancing fibroblast migration at a wound site which includes contacting the wound site with a fibrinogen preparation which includes a lipid rich component.

Another aspect of the present invention relates to a composition which includes fibrinogen and a lipid rich component.

Thus, the present invention relates to a method and a composition for enhancing wound healing by enhancing fibroblast migration to the wound site. By enhancing fibroblast migration, wounds that require the rapid formation of new tissue, such as chronic cutaneous ulcers and fresh surgical and traumatic wounds that cannot be closed, can be treated. Fibrinogen preparations that merely act as a blood clotting mechanism cannot achieve this objective.

DETAILED DESCRIPTION OF THE DRAWINGS

DETAILED DESCRIPTION OF THE INVENTION

Figure 1:
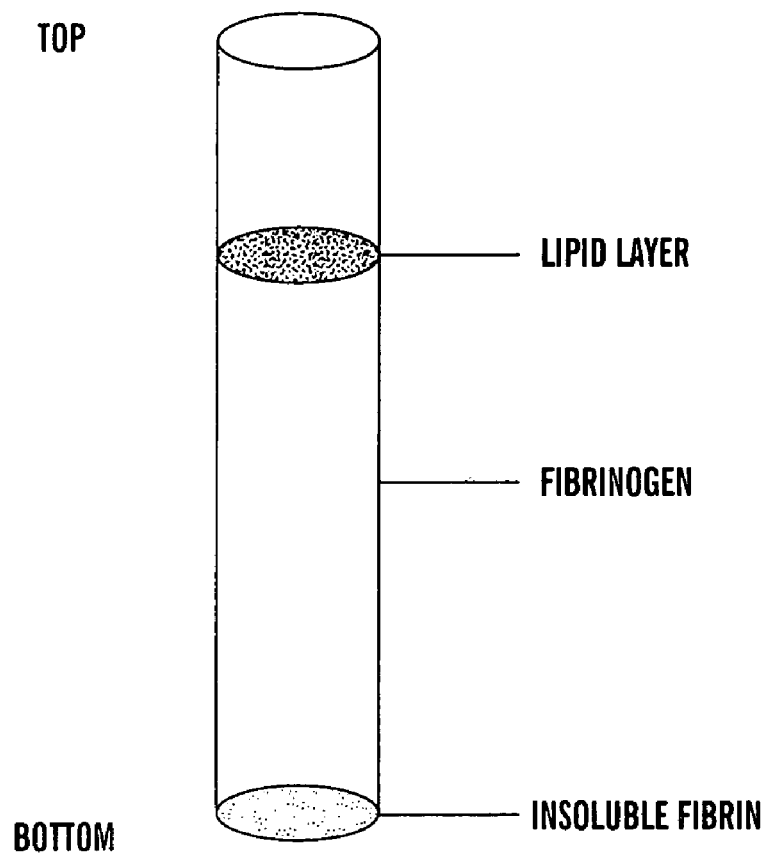
FIG. 1 is a schematic illustration of the three sub-fractions of one embodiment of the fibrinogen preparation of the present invention.

The present invention relates to a method for enhancing fibroblast migration at a wound site. The method includes contacting the wound site with fibrinogen that is prepared by a process which includes using glycine to precipitate fibrinogen from plasma.

Another aspect of the present invention relates to a method for enhancing fibroblast migration at a wound site which includes contacting the wound site with a fibrinogen preparation which includes a lipid rich component.

Another aspect of the present invention relates to a composition which includes fibrinogen and a lipid rich component.

As used herein, "enhancing fibroblast migration" is meant to include any improvement or increase in the movement or mobility of fibroblast cells in a wound. Fibroblast migration can be measured by a variety of methods. One particularly advantageous method is described in U.S. Pat. No. 5,935,850 (the contents of which are hereby incorporated by reference herein); Greiling and Clark (1996); and Greiling and Clark (1997). Briefly, organotypic dermal constructs consisting of human adult dermal fibroblasts embedded in floating type 1 collagen gels are pasted on 24 well tissue culture dishes coated with fibrin fibrils. Fibrin gels are then cast around the "dermal equivalent" forming an "inside-out" wound construct. The number of fibroblast cells that migrate in the presence and absence of various soluble biologic response modifiers (such as the fibrinogen preparations of the present invention) can then be quantified, for example using a Nikon inverted phase microscope, by visually counting identifiable fibroblast cell nuclei located outside of the construct. Preferably, the increase in fibroblast migration produced by contacting the wound with fibrinogen in accordance with the present invention (e.g., $(A-A_o)/A_o$, where A and $A_o$ are the number of identifiable fibroblast cell nuclei located outside of the above-described construct in the presence and absence, respectively, of fibrinogen) is at least about 0.5, more preferably at least about 1.0, and most preferably at least about 1.5.

Further, as used herein, a "wound" and "wound site" are intended to include both acute and chronic dermal wounds including, for example, surgical incisional wounds, traumatic wounds, cancer extirpations, radiation wounds, venous leg ulcers, diabetic ulcers, and pressure ulcers.

The plasma employed in the present invention is collected by conventional methods and, in practice, can be from blood of a single individual, or, alternatively, it can be pooled from multiple individuals. Preferably the plasma is from the same species of animal (e.g., human) as the wound being treated.

As indicated above, fibrinogen is isolated from the plasma by precipitation. In particular, the method of precipitation is achieved with glycine and is carried out in a number of steps.

As a first step, the plasma is precipitated with glycine to produce a precipitate and a supernatant in a manner known to those of ordinary skill in the art. A preferred method is described in Galanakis (1995). Preferably, precipitation is carried out by adding glycine to the plasma in an amount such that the final concentration of glycine in the plasma/glycine mixture is from about 1.0 to about 2.1 M. Preferably, the glycine is added as dry glycine to the mixture. Once the addition is complete, precipitation is allowed to proceed during incubation. Incubation proceeds at temperatures below room temperature (e.g., refrigeration temperatures), preferably from between about 2° C. and about 7° C., more preferably about 5° C. Incubation occurs for from about 30 minutes to about 12 hours, preferably about 1 hour, until the precipitate is formed. In practice, it is most convenient to conduct the precipitation by placing the plasma/glycine mixture in a standard refrigerator (i.e., at about 5° C.). After incubation, a precipitate and a supernatant are produced, which can be separated by conventional methods, such as decanting or, preferably, centrifuging at temperatures from between about 2° C. and about 7° C., preferably about 5° C. The precipitate will contain about 90% of the fibrinogen from the plasma. The purity of the fibrinogen is above 50%.

If a preparation having high purity content is desired, fibrinogen is further isolated from the precipitate of the first step. A high purity content fibrinogen is defined as fibrinogen having a purity content of about or above 99%.

A second step is used to isolate fibrinogen from the precipitate of the first step. As used herein, second step generally refers to the process of adding buffer to a precipitate to produce a mixture, adding glycine to the mixture to produce a precipitate and a supernatant, and separating the precipitate and supernatant. This second step can be repeated as many times as desired.

Typically, the precipitate produced in the first step is dissolved in a suitable buffer to produce a solution. Preferably, the buffer has a pH of from about 6 to about 8, preferably from about 6.2 to about 7.6, most preferably about 6.4. One suitable buffer for carrying out this process contains about 150 mM of sodium chloride, about 10 mM sodium phosphate, and 100 mM epsilon-aminocaproic acid in water, preferably in sterile water suitable for injection. Other buffers suitable in the present invention include 10 mM Tris-HCl (pH 7.4) and 150 mM NaCl. The amount of buffer employed to effect the dissolution is preferably from about 30% to about 40% of the volume of the original plasma used in the first step. That is, if the precipitate is precipitated in the first step from plasma having a volume of V, the buffer used in this second step preferably has a volume of from about 0.3 V to about 0.4 V (i.e., between about 3/10's of V to about 4/10's of V). More preferably, the volume of buffer employed to effect the dissolution of the precipitate is about 35% of the volume of the plasma used in the first step.

Glycine, typically dry (as described above), and at a suitable concentration is then added to the resulting solution in an amount such that the final concentration of glycine in the resulting mixture is from about 1.7 to about 2.2 M and, more preferably, about 2.1 M. The resulting mixture is incubated, preferably at a temperature of from between about 2° C. to about 7° C., most preferably at about 5° C., for from about 30 minutes to about 2 hours, preferably for about one hour.

As a result, a precipitate and supernatant form, which are separated, preferably by centrifugation at from between about 2° C. to about 7° C., most preferably at about 5° C.

This second step is advantageously repeated several times. Preferably, the second step is repeated at least twice. The precipitate at the end of the second step will contain about 60% of the fibrinogen from the plasma. The fibrinogen is at a purity of about 90%.

To produce fibrinogen having a low purity content, fibrinogen can be additionally or alternatively isolated from the supernatant (instead of the precipitate) of the original plasma/glycine mixture of the first step in a manner similar to that described above. As used herein, low purity fibrinogen means fibrinogen having a purity content of about or above 95%, but below 99%. The low purity fibrinogen is produced by adding glycine, typically dry and at a suitable concentration, to the supernatant of the first step to produce a mixture. The resulting mixture is incubated, preferably at refrigerator temperatures, for about 1 hour. As a result, a precipitate and supernatant form, which are separated, preferably by centrifugation at refrigerator temperatures. The precipitate can then be dissolved in an appropriate buffer (e.g., the ones described above), glycine added (preferably to a final glycine concentration of about 2.1 M), the mixture incubated, and the resulting precipitate separated. This process can be repeated several times.

Irrespective of whether the fibrinogen is isolated as a precipitate from the precipitate or supernatant or both of the original plasma/glycine mixture described above, the precipitate can be advantageously further treated to purify the fibrinogen. Typically, the further treatment includes dissolving the precipitate resulting from the glycine precipitation(s) described above in an appropriate buffer (e.g., as described above) to produce a solution where the precipitate is present in a volume of ½ to ⅓ of the original plasma, with ⅓ being especially preferred, and precipitating this solution. Preferably, the precipitation is achieved by adding a compound such as ammonium sulfate to the solution. Typically, the ammonium sulfate is added as a saturated solution, and the amount of ammonium sulfate in the solution is about 25 percent of its saturation level. The resulting solution is redissolved in a suitable buffer (as described above) and reprecipited, preferably with dialysis in 0.3 M NaCl.

Using the method of the present invention, a precipitate fraction of fibrinogen with a purity of greater than 95% (as ascertained by SDS-polyacrylamide gel electrophoresis ("SDS-PAGE")) is obtained. When high purity fibrinogen is desired, using the method of the present invention fibrinogen having a purity of about or above 99% is obtained.

In addition, a lipid rich fraction is obtained. The lipid rich solids are found floating in the final supernatant produced by either method described above. The lipid rich solids are separated from the final supernatant (typically by centrifugation), added to a suitable buffer (as described above) and reprecipited, preferably with dialysis in 0.3 M NaCl, and treated with 25% saturated ammonium sulfate (as described above). The precipitate from this step is discarded and the resultant supernatant is rich in plasma lipids. This supernatant which includes lipids is called the lipid rich component. Although not meaning to be bound by theory, the lipids contained in the lipid rich component result in enhanced fibroblast migration when applied to a wound. Alternatively, proteins bound to the lipids of the lipid rich layer result in enhanced fibroblast migration when applied to a wound.

Once prepared in the above-described manner, the fibrinogen and the lipid rich component are stored, preferably at from about −50° C. to about −80° C. Prior to use, they can be thawed, for example at 37° C.

The fibrinogen prepared in accordance with the above-described methods enhances fibroblast migration during wound healing and, thus, enhances wound healing. Further, the lipid rich component enhances fibroblast migration during wound healing.

Enhancement of wound healing refers to the traditional sense of wound healing where clean closure of the wound occurs. Since naturally occurring wound healing involves the movement of fibroblasts into the wound site, enhancement of wound healing can be assayed in vitro using the model for cell transmigration provided in U.S. Pat. No. 5,935,850 (the contents of which are incorporated by reference herein), Greiling and Clark (1996), and Greiling and Clark (1997). Briefly, the model provides a contracted collagen gel containing fibroblasts surrounded by a fibrin gel. When fibrinogen prepared as described above is contacted with the fibrin gel, fibroblast movement from the collagen gel into the fibrin gel is enhanced.

Accordingly, the above described method of enhancing migration of fibroblasts at a wound site can advantageously further include contacting the wound site with other materials which promote wound healing. Such contacting with other materials that promote wound healing can occur prior to, during, and/or after the wound site is contacted with fibrinogen. For example, the wound site can be contacted with a growth factor (such as platelet-derived growth factor ("PDGF") (described in, for example, Seppa et al. (1982) and in Senior et al. (1985)) or an extracellular matrix material (such as, fibronectin and hyaluronan). Preferably, the wound site is contacted with fibronectin in addition to fibrinogen prepared by the process described above. In a preferred embodiment, fibronectin is added to the fibrinogen by mixing the fibronectin with the fibrinogen. Alternatively, the wound site can be contacted with more than one growth factor, more than one extracellular matrix material, or combinations of growth factor(s) and extracellular matrix material(s). Advantageously, the wound site is contacted with the lipid rich component. The wound site can be contacted with the lipid rich component either alone or in combination with fibrinogen, one or more growth factors, one or more extracellular matrix materials or a combination thereof.

The fibrinogen prepared as described above (with or without the lipid rich component) can be contacted with the wound site by incorporating it in a fibrinogen preparation and then contacting the fibrinogen preparation with the wound site. The fibrinogen preparation generally contains fibrinogen which enhances fibroblast migration. In addition, inert additives may be incorporated into the fibrinogen preparation. These include preservatives, dispersants, diluents, and other physiologically compatible materials. Where the fibrinogen is to be used concurrently with growth factor(s), extracellular material(s), or combinations thereof, the growth factor(s) and/or extracellular matrix material(s) can advantageously be incorporated in the fibrinogen preparation. Alternatively, the fibrinogen, lipid rich component, growth factors, extracellular materials, or combinations thereof can be contacted with the wound site separately.

In cases where the wound to be treated is bleeding, the fibrinogen preparation can further include thrombin so that the fibrinogen preparation, in addition to enhancing fibroblast migration, also promotes blood clotting. However, unlike conventional fibrinogen preparations, the fibrinogen preparation of the present invention (i.e., the fibrinogen preparation containing fibrinogen prepared as described above) has utility even if it is substantially free of thrombin, because it is useful for promoting fibroblast migration in all wounds, including in wounds that are not bleeding. As used herein, wounds that are not bleeding are meant to include wounds that may be oozing blood but that would not be considered by the skilled clinician as requiring intervention to induce or promote clotting. Fibrinogen preparations that are substantially free of thrombin are meant to include preparations in which the thrombin level is below the level which is generally viewed as being necessary to promote clotting when used in conjunction with fibrinogen. Examples of fibrinogen preparations that are substantially free of thrombin include fibrinogen preparations in which the weight-to-weight ratio of thrombin to fibrinogen is less than 1, less that 0.8, less than 0.5, less than 0.3, or less than 0.1.

As indicated above the fibrinogen or fibrinogen preparation of the present invention is contacted with the wound or wound site. Contacting can be carried out by any suitable method. For example the fibrinogen or fibrinogen preparation can be delivered to the wound site via a syringe or pipet or by spraying or misting fibrinogen or fibrinogen preparation onto the wound. Lyophilized fibrinogen or fibrinogen preparation can be used directly in powdered form, for example by sprinkling the powder on the wound. Alternatively, the fibrinogen or fibrinogen preparation can be applied to the wound by incorporating it in a gauze pad, sponge, collagen or gel-type matrix and then applying the gauze pad, sponge, collagen or gel-type matrix to the wound. As explained above, the fibrinogen or fibrinogen preparation of the present application can be contacted with wounds that are bleeding or with wounds that are not bleeding. For example, the fibrinogen or fibrinogen preparation of the present application can be first contacted with the wound while the wound is bleeding and said contacting can be continued after bleeding ceases. For purposes of the present application, the contact which is maintained subsequent to cessation of bleeding is to be considered to be a contact with a non-bleeding wound. Alternatively, the fibrinogen or fibrinogen preparation of the present application can be contacted with a wound only after bleeding from the wound stops.

The amount of fibrinogen or fibrinogen preparation to be applied to the wound depends on a variety of factors, such as the size of the treatment site, the nature and condition of the wound in need of treatment, and factors that might be unique to the patient being treated. The optimal therapeutic amount for a specific wound can be determined by contacting the wound site with various concentrations of fibrinogen or fibrinogen preparation and observing the effect on wound healing.

The present invention is further illustrated by the following examples.

EXAMPLES

Materials and Methods

Fibrinogen Preparations from Precipitate

The fibrinogen preparations of the present invention were prepared from a 1M glycine precipitation formed in the cold (4° C.) that had been discarded in a previously described procedure (Galanakis (1995)). In particular, glycine was dissolved in pooled human plasma to attain 1 M final concentration and the mixture was allowed to stand on ice for at least one hour. By subsequent centrifugation at 5° C., two fractions were obtained: the precipitate and the supernatant. The precipitate obtained from plasma containing 1 M glycine, 5° C., was redissolved (pH 6.4) and re-precipitated twice with 2.1 M glycine, 5° C. The precipitate was then dissolved, precipitated with $(NH_4)_2SO_4$ to 25% saturation, redissolved and exhaustively dialyzed vs. 0.3M NaCl. The final product was stored at −80° C. Greater than 95% purity was ascertained by SDS-polyacrylamide gel electrophoresis (SDS-PAGE). The gels also disclosed the expected doublet of fibrinogen bands I and II indicating that these bands did not differ from those of fibrinogen in unfractionated plasma.

Fibrinogen Preparations from Supernatant

The following preparations were purified from the supernatant produced during precipitation of the fibrinogen precipitate described above.

Sample 1 was isolated as previously described (Galanakis (1995)). It was the purest fibrinogen isolate. It had virtually all its alpha chains intact but lacked molecules with gamma chains that have an extended carboxy terminal which constitute approximately 15% of the fibrinogen in plasma. The extended gamma chains are from a splicing mRNA variant. It extends the gamma chain by deleting the last two amino acids of the regular gamma chain and extending it with a 20 amino acid segment.

Sample 2 was isolated by a modification (Galanakis (1995)) of the procedure of Mosesson and Sherry (1966). Sample 2 was a highly pure fibrinogen isolate, but less pure than Sample 1, in that a minute contaminant of Factor XIII was detectable by biologic activity. It also had virtually all of its alpha chains intact and contained molecules with both extended and non-extended gamma chains.

Sample 3 was the same as Sample 2, but was enriched with soluble fibrin. Fibrin monomer was prepared as described in Galanakis et al. (1987). An amount of fibrin monomer (from a stock solution of 20 to 30 mg/ml, pH 4.5) was added to exceed 10% (mg/mg) of fibrinogen in solution, allowed to equilibrate at 37° C. and any clot that formed was removed. The resulting fibrinogen solution was termed fibrin-saturated and used. Care was taken to ascertain that the pH of the fibrinogen solution remained above 6 in storage and during clotting.

Sample 4 was isolated by a modification (Galanakis (1995)) of the procedure of Mosesson and Sherry (1966). Sample 4 had a purity similar to that of Sample 3, but contained a major population of molecules (approx. 20 to 30%) which were clottable but had degraded alpha chains.

Sample 5 was isolated by a modification (Galanakis (1995)) of the procedure of Mosesson and Sherry (1966). Sample 5 was similar to Sample 4 in structure but less pure in that trace, but detectable, amounts of fibronectin and factor XIII were present.

Sample 6 was similar in all respects to Sample 5, with the exception of being enriched with soluble fibrin. Fibrin monomer was prepared and added to Sample 5 as described above for Sample 3.

Sample 7 was isolated from the supernatant produced in Sample 1 above. It contained only minor amounts of fibrinogen, but was rich in plasma lipids.

Normal Human Dermal Fibroblasts

Primary cultures of human adult dermal fibroblasts, acquired from Marcia Simon (Living Skin Bank, SUNY at Stony Brook), the ATCC (Bethesda, Md.), or the NIA (Bethesda, Md.), were cultured in Dulbecco's Modified Eagle's Medium (DMEM, Life Technologies) containing 42 mM sodium bicarbonate and supplemented with 100 U/ml penicillin, 100 µg/ml streptomycin, and 10% fetal bovine serum (FBS, HyClone, Logan, Utah) at 37° C. and 5% $CO_2$/95% air in a humidified atmosphere.

Preparation of Floating Contracted Collagen Gels

Fibroblast cultures at 80% confluence were harvested by treatment with a 0.05% trypsin/0.01% EDTA. Trypsin is inactivated by addition of soy bean trypsin inhibitor in PBS containing 0.2% BSA. The cells are washed twice with DMEM+2% BSA and resuspended at a concentration of $1 \times 10^6$ cells/ml. The fibroblasts are mixed with neutralized collagen (Vitrogen 100, Celtrix Labs., Santa Clara, Calif.), 2% BSA, 30 ng/ml PDGF-BB, 30 µg/ml fibronectin, and concentrated DMEM so that the final concentration of DMEM and sodium bicarbonate is 1×. 600 µl of the cell mixture is added to the wells of a 24-well tissue culture plate, which has been precoated with 2% BSA. The collagen is allowed to polymerize at 37° C. The final concentration of collagen is 1.8 mg/ml and each gel contains $6 \times 10^4$ cells. After two hours incubation, the gels are gently detached from the plastic surface to allow contraction with the addition of 0.5 ml DMEM+2% BSA and 30 ng/ml PDGF-BB per well. The gels are incubated overnight at 37° C. in 100% humidity, 5% $CO_2$ and 95% air.

Preparation of the Three-Dimensional Transmigration Model

As described in Greiling and Clark (1997), dried fibrin fibril-coated dishes are washed once with PBS and fibroblast-contracted collagen gels are placed on the surface. Fibrinogen, as produced by the method of the present invention (or as a comparison sample) at a final concentration of 300 µg/ml is mixed with DMEM and 1.0 U/ml thrombin, added to the wells so that the solution is level with the top of the collagen gel, and allowed to clot at room temperature for 30 minutes. When needed, other supplements, such as 30 ng/ml PDGF-BB, are added to the mixture. The migration assays are quantified after a 24 hour incubation period at 37° C. in 100% humidity, 5% $CO_2$ and 95% air.

Evaluation of Cell Migration

The number of migrated cells was quantified under a Nikon inverted phase microscope by visually counting identifiable cell nuclei located outside of the contracted collagen gel in the fibrin gel. Within a given experiment, each condition was run in triplicate and means±SD calculated. All experiments were repeated at least three times. Statistical differences among conditions can be determined by ANOVA.

Example 1

The fibrinogen preparations described above were tested to determine if fibroblast migration was enhanced by the fibrinogen preparation of the present invention.

Results

The preparations were tested using the three-dimensional transmigration assay described above and in Greiling and Clark (1997). While preparations of the present invention (i.e. produced from the precipitate), when clotted, were found to permit fibroblast migration, most preparations from the supernatant had little or no activity. A crude preparation of fibrinogen obtained from Calbiochem was used as a control in these assays. This commercial laboratory grade fibrinogen was also used in the study on fibroblast migration through fibrin gels (Greiling and Clark (1997)). The activity in Sample 4 was intrinsically unstable as it was lost after 2 freeze/thaw cycles. Although little activity was found in Sample 5, this fraction had relatively good activity when saturated with fibrin monomers. Although these data suggest that the activity is attributable to fibrin monomer, when another aliquot of the same fibrin monomer preparation was added to Sample 2, no activity was observed. The presence or absence of fibronectin in these fibrinogen preparations was not responsible for their differential activity, because fibronectin was always added to the fibrinogen at the time of assay. In addition, whether Factor XIII was responsible for the activity was examined. When the plasma transglutaminase (Calbiochem) was added to Sample 1 fibrinogen (100 nM Factor XIII/M fibrinogen), no discernable activity was observed. A real possibility is that two or more factors, in addition to fibronectin, are necessary for fibroblast migration. For example, perhaps both Factor XIII and fibrin monomers may be necessary for migration.

Discussion

During fibrinogen isolation from plasma, a relatively low solubility fraction can be harvested with 1M glycine that is fibrin-rich and contains other proteins with low solubility. In typical fibrinogen purification schemes, however, this fraction is usually discarded because it is not readily soluble in physiologic buffer systems. It has been used, however, to isolate other proteins including fibronectin, Factor VIII and Factor XIII. Although there are alternative ways to obtain low solubility proteins from plasma, (e.g. plasma cryoprecipitation, differential or graduated ethanol precipitation at very low temperatures, salting out by various precipitants such as glycine, beta alanine, and ether) the present invention focuses on the fibrinogen isolate from the precipitate, since it is the only low solubility protein fraction from plasma which supports fibroblast migration. In addition, the present invention is directed to the lipid rich component, which also supports fibroblast migration.

Although an explosion of information on the molecular and cellular biology of wound repair has accumulated over the past decade (Clark (1996b)), surprisingly little was known about the induction of new tissue, called granulation tissue, a critical event in the healing process. Recently several seminal observations about new tissue formation in wounds were made (Greiling and Clark (1997); Gailit et al. (1996); Gailit and Clark (1996); McClain et al. (1996); Xu et al. (1996); Gailit et al (1997)). This information has been used to develop a fibrin matrix composite that promotes fibroblast recruitment from an adjacent collagenous matrix (Greiling and Clark (1997)). This matrix has potential for use in freshly debrided chronic cutaneous ulcers and fresh surgical and traumatic wounds that cannot be closed.

During the first few days after injury, a fibrin clot is deposited in the wound space (Welch et al. (1990)). The clot contains fibrin, fibronectin and vitronectin which together provide a provisional matrix scaffold for the movement of recruited cells into the wound space (Greiling and Clark (1997); Clark (1993a); Clark (1993b)). Concomitantly, platelets release a plethora of growth factors including the potent mesenchymal cell mitogen, platelet-derived growth factor (PDGF) (Heldin et al. (1996)). Subsequently, blood leukocytes, especially neutrophils and monocytes, migrate into the fibrin-rich provisional matrix. As monocytes mature into macrophages they begin to produce growth factors, including PDGF-BB, which are added to the wound space milieu (Rappolee et al. (1988); Shaw et al. (1990)). In response to these growth factors, fibroblasts in the underlying subcutaneous tissue, and in the adjacent dermis, to a lesser extent, proliferate (Clark (1993a)). Endothelial cells within blood vessels adjacent to the wound also proliferate, causing marked vessel hypertrophy (Clark et al (1982a); Clark et al. (1982b)). Despite the remarkable cell proliferation in the tissue surrounding the wound, no mesenchymal invasion of the fibrin clot was observed for the first three days after injury (Welch et al. (1990); Clark et al. (1995)). On the fourth day fibroblasts and endothelial cells invade the fibrin clot-filled wound as an organized tissue construct called granulation tissue. Fibroblasts of the granulation tissue appear bound together with a fibronectin meshwork; and endothelial cells organize into capillaries that intercalate the interwoven fibroblast aggregate in a vertical array (Clark (1993a)). Despite the clear clinical importance of this early stage of wound healing, little is known about the inductive processes leading to granulation tissue formation.

Chronic ulcers, in contrast to acute wounds, fail to heal. Here the problem appears to be a corrupted provisional matrix. The fibrin provisional matrix in the ulcer bed interstitium fails to support healing possibly because it becomes partially degraded (Bini et al. (1989)), excessively crosslinked (Brommer et al. (1992)) or stripped of other molecules important for wound healing such as fibronectin (Herrick et al. (1992)). In fact, based on in vitro data, fibronectin is critical for cell invasion of the fibrin clot (Greiling and Clark (1997)). To simulate fibroblast movement from periwound collagenous stroma into provisional matrix-filled wound space, a contracted collagen gel containing skin fibroblasts was pasted onto a surface of fibrin fibrils and surrounded by a fibrin clot (Greiling and Clark (1997)). This forms an "inside-out" wound environment. To further simulate the in vivo situation, 30 ng/ml PDGF was added to the fibrin clot. Fibroblast appearance in the translucent fibrin gel was quantified by cell counts. Cell accumulation in the fibrin gel was attributable to migration rather than mitogenesis as judged by the movement of nonproliferating, irradiated cells. Transmigration from the collagen gel into fibrin required fibronectin in both matrices. In addition, migration was dependent on both $\alpha5\beta1$ and $\alpha v\beta3$ provisional matrix integrins (Greiling and Clark (1997)). Thus, the absence of fibronectin in the wound provisional matrix of chronic ulcers (Herrick et al. (1992)) may directly hinder tissue cell repopulation of the wound. This possibility has been supported in fresh porcine wounds to which exogenous fibrin without fibronectin has been added. Relatively few cells moved into these wounds compared to wounds receiving fibrin replete with fibronectin. Thus, one of the fundamental reasons that a fresh surgical or traumatic gaping wound heals faster than a chronic ulcer may be that the former has a fibrin matrix with abundant fibronectin (Clark et al. (1982)) while the latter has little or no fibronectin in the provisional matrix (Herrick et al. (1992)).

Using the 3-dimensional transmigration assay described in U.S. Pat. No. 5,935,850, (which is hereby incorporated by reference herein), it was discovered that human dermal fibroblast movement from a collagen gel to a fibronectin replete-fibrin clot requires a special preparation of fibrinogen containing fibronectin (Greiling and Clark (1997)). A number of fibrinogen isolates acquired by various isolation procedures, were clotted and tested for their ability to allow fibroblast migration through a 3-dimensional fibrin clot (Greiling and Clark (1997)). Fibronectin at a 1:10 molar ratio to fibrinogen and 30 to 100 ng/ml PDGF were added to the fibrinogen just prior to clotting with human thrombin as previously described to result in maximal cell migration (Greiling and Clark (1997)).

Example 2

As a first step toward characterization, quality control experiments were done on the activity of sequential fibrinogen isolates from the 1M glycine precipitates produced and examined in Example 1. Two sets of fibrinogen isolates were prepared from the 1M glycine precipitate. Each isolate was made from 2–5 normal donor plasma pools. Fibroblast migration occurred in fibrin gels made from three of six isolates in the first set and four of four isolates in the second set. In the first set, those with low or no activity had a low fibrinogen concentration (i.e. <8 mg/ml). Consequently, they could not be re-tested to confirm their low activity. In the preparation of the second set of isolates, care was taken to obtain fibrinogen concentrations >10 mg/ml and enough material to retest many times. All four preparations from this set gave fibrin gels that permitted fibroblasts migration. On first testing, one of the four isolates showed low migration activity, but another aliquot of this same isolate had activity equivalent to the other three. The aliquot that did not have activity had been stored at the top of a −80° C. freezer and may have undergone repeated partial thawing prior to testing.

Example 3

Empirical observations have shown that a fibroblast migration enhancement (FME) property is present in fibrinogen preparations of relatively low purity and this activity is stable on freeze thawing of such preparations. Conversely, fibrinogen preparations that are of the highest possible purity, such as fibrinogen fraction I-4, DEAEc peak 1 fraction, and others (produced by methods known to those skilled in the art) either possess low or no activity. Of particular use is fraction I-4, which can be prepared in bulk and whose moderate FME activity progressively decreases on repeat freeze thawing, thus enabling its use as a negative control. In the discussion below, positive and negative controls are termed C1 and C2, respectively. Fibrinogen isolates with high activity are isolated from plasma by procedures that yield two kinds of active isolates, one enriched with soluble fibrin and the other lacking fibrin enrichment. The procedures also yield a lipid or lipoprotein rich (L) component which is enriched in FME activity.

Fibrin-Rich Fibrinogen Preparation.

Glycine is dissolved in plasma to 1 M (or 1 molar) concentration and allowed to stand at 4° C. overnight. The precipitate formed is dissolved in phosphate buffered saline, pH 6.4, subjected to reprecipitation with 2.1 M Glycine at 4° C., and this step is repeated. An additional precipitation step is performed with either 2.1 M Gly or 25% saturated Ammonium Sulfate. The fibrinogen isolate thus obtained is dialyzed vs 0.3 M NaCl at 4° C. and termed 2F. As shown below, fibrinogen 2F may be further separated into sub-fractions. A large amount of insoluble fibrin gel forms during dialysis, and this is removed by centrifugation as described below.

Fibrinogen Low in Fibrin Content Preparation.

An isolate is obtained from the plasma supernatant of the initial 1 M Gly step detailed in the paragraph above. For this purpose, additional Glycine is added and dissolved to achieve 2.1 M Gly concentration and the precipitate obtained at 4° C. is subjected to the same precipitation steps described above. The final isolate is dialyzed as above and termed 2H. As shown below, fibrinogen 2H may be further separated into sub-fractions. During dialysis a small amount of insoluble fibrin forms and is removed by centrifugation as described in the paragraph below.

Further Sub-Fractionation to Obtain and Characterize Sub-Fractions.

Each of the fractions, 2F and 2H, is subjected to centrifugation using at least 4000 XG for 30 or more minutes at 4° C. The resulting three sub-fractions are illustrated in FIG. 1. One sub-fraction is a lipid or lipoprotein component which contains insoluble material floating at the top of the solution. This subfraction is termed 2FL (from the 2F fibrin rich fraction) or 2HL (from the 2H low fibrin content fraction). Use of a spatula or other implement permits harvesting these sub-fractions. The second sub-fraction is the bulk of isolated fibrinogen and is referred to herein as 2F sub-fraction (fibrin rich fibrinogen) or 2H sub-fraction (low fibrin content fibrinogen). The third sub-fraction is a pellet at the bottom of the centrifuged solution, which consists of insoluble fibrin gel and is discarded. During the harvest and testing of the lipid and fibrinogen sub-fractions certain characteristics emerge. One is that fibrinogen 2H invariably contains major amounts of sub-fraction 2HL, and fibrinogen 2F, by contrast, tends to contain lower amounts of sub-fraction 2FL. Such differences are demonstrable by dissolving the material and measuring its turbidity. Further, some 2FL sub-fractions are of substantial amounts while others are of very small amounts compared to those in the 2HL counterparts from the same starting plasma. A constellation of characteristics of the L isolates is their self-evident low density and coalescence into insoluble floating sheets or particles following centrifugation, their yellowish-white and opaque appearance on visual inspection (particularly marked in 2HL), their capacity to be readily dispersed and re-dissolved in fibrinogen containing buffers, and their high turbidity when re-dissolved and assessed spectrophotometrically.

To compare the FME activity of 2HL or 2FL with their 2H or 2F counterparts, fibrin is formed in the assay from the same lot. Comparison can also be made with the same parent (or uncentrifuged fibrinogen preparation). In order to test the L moiety of 2FL or 2HL alone, fibrinogen can be removed so that the sub-fraction can be tested without its parent fibrinogen. To remove its fibrinogen, ammonium sulfate is added to 25% saturation and the precipitate is discarded. The floating insoluble material on the top of the solution is then harvested and dialyzed.

An Alternate Method to Sub-Fractionate 2F or 2H Isolates.

Figure 2:
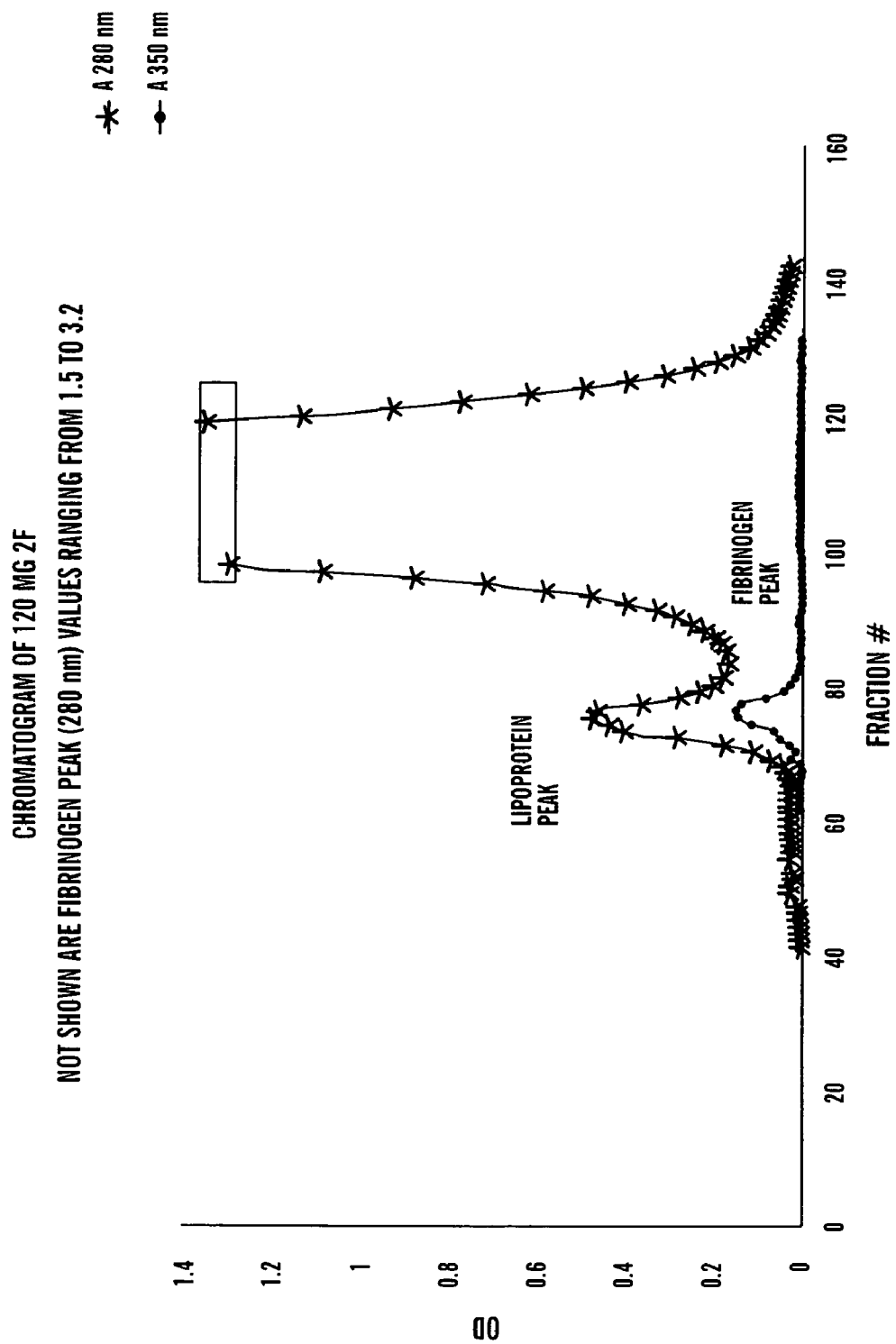
FIG. 2 is a chromatogram illustrating the fibrinogen peak and lipoprotein peak of a preparation of the present invention.

The fractions can be sub-fractionated by subjecting them to size exclusion chromatography, as shown in FIG. 2. This enables removal of most of the lipid and of the soluble fibrin components, so that each such component can be tested. Absorbance values of the eluting fractions are obtained at 280 nm and at 350 nm. Absorbance at 280 nm reflects the presence of protein and that at 350 nm reflects light scattering and, thus, the opacity caused by the lipid content of the fibrinogen solution. This chromatographic procedure results in an early elution peak, labeled peak I. Fractions containing this peak appear white-opaque, show high absorbance values at 350 nm as expected, and show the presence of protein by their absorbance values at 280 nm. When dialyzed against water and freeze dried, this peak is insoluble in buffer but can be resolubilized at least in part in fibrinogen or other protein solutions. The second peak, labeled peak II, consists of fibrinogen and soluble fibrin. This peak shows absorbance at 280 nm but little or negligible absorbance at 350 nm, as shown, and constitutes the bulk of protein applied to the column.

Fibroblast Enhancing (FME) Activity: 2F, 2H and Non-Chromatographic Subfractions.

Figure 3:
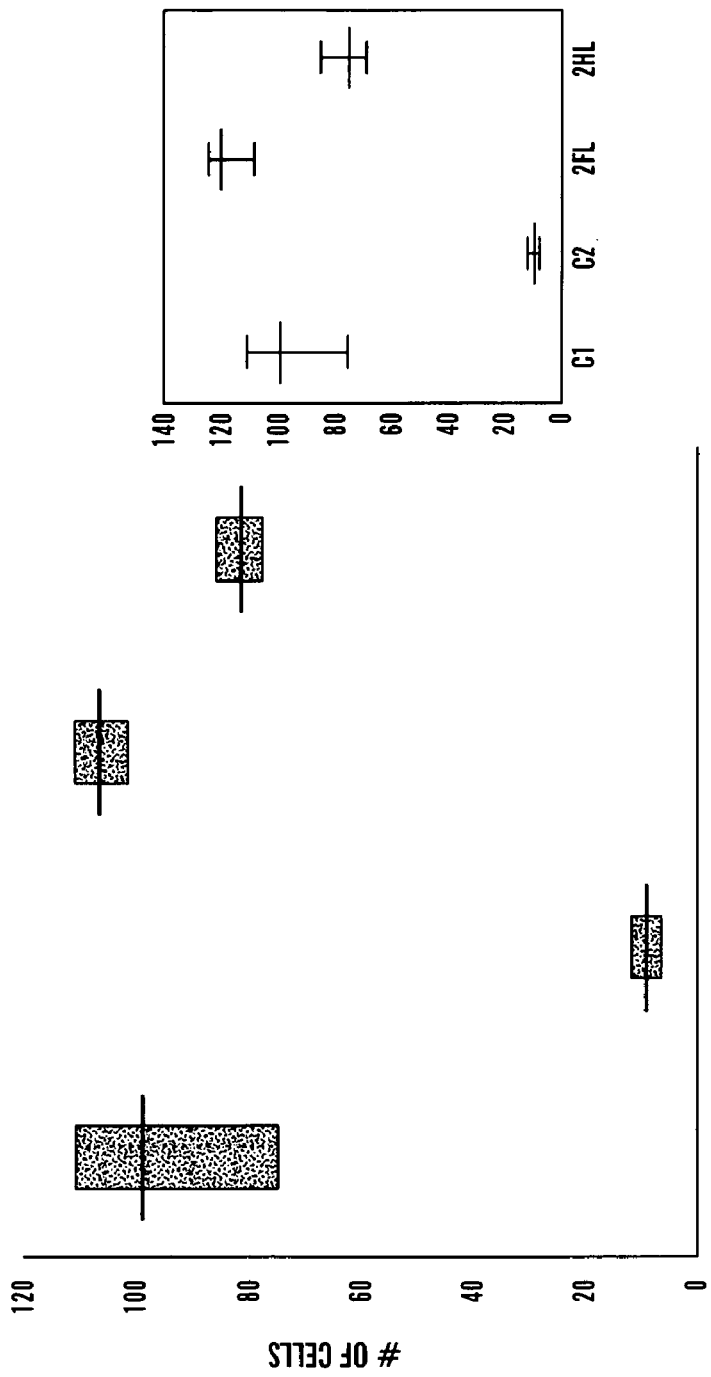
FIG. 3 is a comparison of the effect on fibroblast migration of fibrinogen isolates C1 (positive control), C2 (negative control), 2H, 2F, 2HL and 2FL.

Fractions 2F and 2H have ample activity, with 2H showing moderately higher activity than 2F. Similarly, this activity remains high, as shown in FIG. 3, in both the L rich subfractions (2FL, 2HL) and fibrin rich sub-fractions (2H, 2F). Moreover, these sub-fractions, 2FL and 2HL, show similarly high activity (See FIG. 3 insert) and this activity remains when fibrinogen is removed from 2HL and 2FL (not shown). Because insoluble lipid in 2HL may induce formation of an abnormal fibrin matrix, care is taken to avoid insoluble lipid aggregates when using 2HL. This is not the case with 2FL, which contains a much lower lipid content and lacks such large insoluble aggregates.

Fibroblast Enhancing (FME) Activity: Chromatographic Subfractions.

Figure 4:
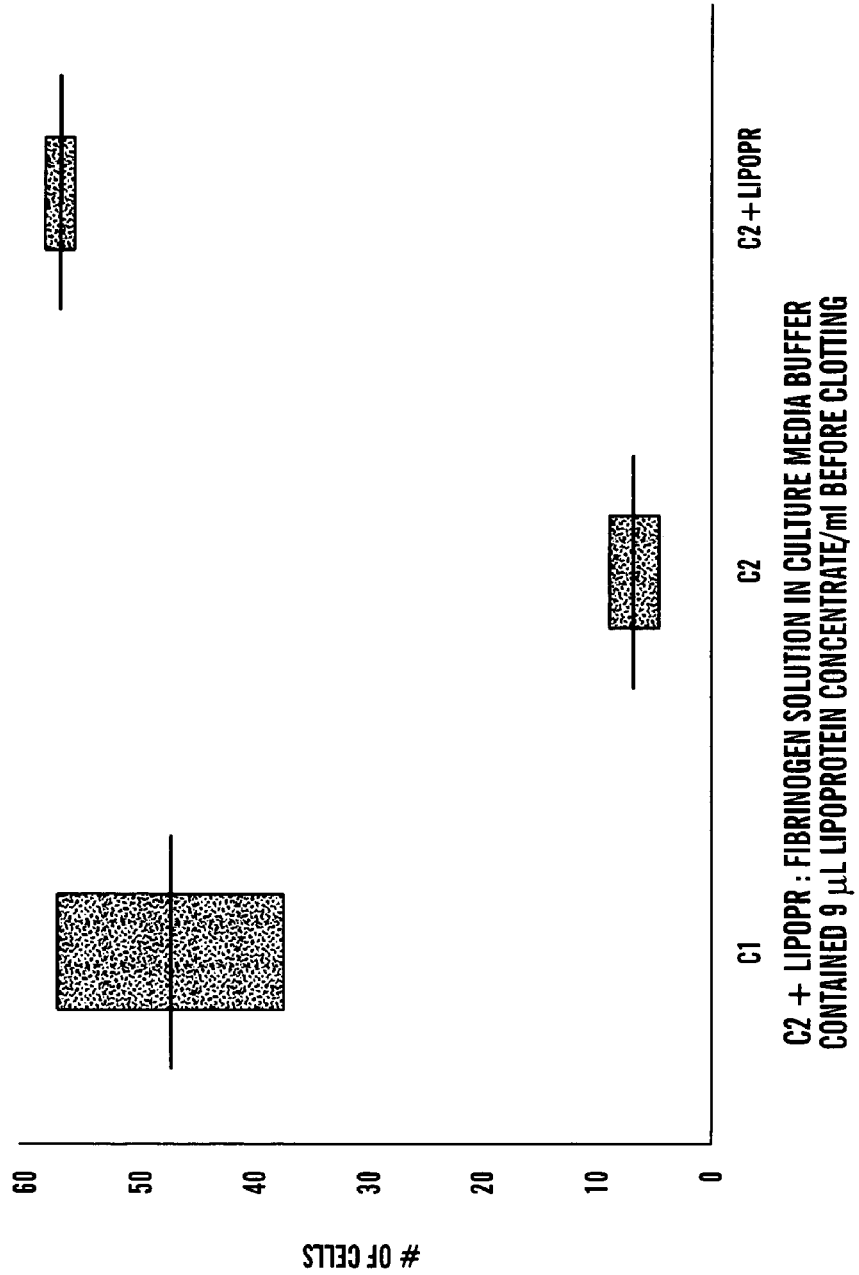
FIG. 4 illustrates the fibroblast migration activity of the lipoprotein peak of FIG. 2.

Tested as outlined above, both peaks (shown in FIG. 2) possess substantial fibroblast migration enhancing activity. The fibroblast migration activity of the lipoprotein (L) peak of FIG. 2 is shown in the FIG. 4. This is consistent with the results from the post-centrifugation sub-fractions described above, indicating that the activity is present both in the L rich and the fibrinogen (L poor) peaks. Considering the small amount of L sub-fraction required to demonstrate the activity, this implies the lipid in these isolates contains relatively higher activity than does fibrinogen per se. That is to say, the activity is more lipophilic than fibrinogenophilic. Moreover, when fibrin-rich fibrinogen was isolated from the ascending limb of the chromatogram it too displayed substantial activity, not shown, consistent with the fact that fraction 2F is fibrin rich and shows activity comparable to 2H.

SUMMARY AND CONCLUSIONS

The fibroblast migration enhancement activity of fibrinogen isolated by the above procedures is associated with three components or sub-fractions: fibrin rich fibrinogen, lipid rich fibrinogen, and fibrinogen not enriched with either fibrin or lipid. Although lipid rich fibrinogen (2FL or 2HL) displays somewhat higher activity, this activity remained when the lipid component was rendered free of fibrinogen by chromatography or other means. Moreover, fibrin rich fibrinogen which is also rendered lipid poor clearly retains its high activity. In another set of observations (data not shown), this activity is progressively lost by freeze thawing of I-4, and absent in DEAEc pure fibrinogen. Taken together, these results imply a non-fibrinogen and possibly non-lipid hydrophobic agent whose FME activity remains stable in storage of fibrinogen/lipid mixtures. This explains its stability in fibrinogen isolates of relatively low purity (i.e. $\geq 95\%$ by protein measurements), and enables potential use of such preparations in situations where enhancement of wound healing is clinically important. Also, in order for fibrinogen isolates to possess the highest FME activity they need be enriched with substantial amounts of a lipid component that co-isolates with them from normal plasma and results also in stability of this activity when fibrinogen is stored frozen and re-frozen. What is more, the lipid component can be isolated and re-introduced into fibrinogen of high purity or any other fibrinogen isolate for the purpose of further enriching its FME activity. This discovery makes it possible to monitor the amounts of this lipid component in any fibrinogen and/or soluble fibrin preparations.

Although the invention has been described in detail for the purpose of illustration, it is understood that such detail is solely for that purpose, and variations can be made therein by those skilled in the art without departing from the spirit and scope of the invention which is defined by the following claims.

REFERENCES

Abraham, J. A., and Klagsbrun, M., in "The Molecular and Cellular Biology of Wound Repair", 2d edition, Clark, R. A. F., ed, Plenum Press, New York, N.Y. (1996).
Bartold, P. M., and Raben, A., *J. Periodontal Research*, 31(3):205–216 (1996).
Bergstrom, N., et al., "Treatment of Pressure Ulcers", U.S. Department of Health and Human Services, Clinical Practice Guideline, Vol. 15, Rockville, Md. (1994).
Bini, A., et al., *Lab. Invest.*, 60:814–821 (1989).
Borgognoni, L., et al., *Euro. J. Dermatology*, 6(2):127–131 (1996).
Boyce, S. T., et al., *Ann. Surg.*, 222:743–752 (1995).
Brennan, M., *Blood Rev.*, 5:240–44 (1991).
Brommer, E. J. P., and van Bocke, L. J. H., *Blood Coag. Fibrinol.*, 3:717 (1992).
Brown, G. L., et al., *N. Eng. J. Med.*, 321:76–79 (1989).
Byrne et al., *J. R. Coll. Surg. Edinb.* 37:394–98 (1992).
Callam, M. J., et al., *Br. Med. J.*, 294:1389–1391 (1987).
Clark, R. A. F., et al., *J. Cell Sci.*, 108:1251–1261 (1995).
Clark, R. A. F., *Am. J. Med. Sci.*, 306:42–48 (1993a).
Clark, R. A. F., in "Dermatology in General Medicine" Fitzpatrick, T. B. et al., eds. McGraw-Hill Book Company, New York, 473–483 (1993b).
Clark, R. A. F., et al., *J. Invest. Dermatol.*, 79:264–269 (1982a).
Clark, R. A. F., et al., *J. Invest. Dermatol.*, 79:269–276 (1982b).
Devries, H. J. C., et al., *Laboratory Investigation*, 73(4):532–540 (1995).
Ellis, D. L., and Yannas, I. V., *Biomaterials*, 17(3):291–299 (1996).
Gailit, J., et al., *Exp. Cell Res.*, 232:118–126 (1997).
Gailit, J., et al., *J. Cell. Physiol.*, 169:281–289 (1996a).
Gailit, J., and Clark, R. A. F., *J. Invest. Dermatol.*, 106:102–108 (1996b).
Galanakis, D. K., *Thromb. Res.*, 78:303–313 (1995).
Galanakis, D. K., et al., *Biochemistry*, 26:2389–2400 (1987).
Gleich et al., *Laryngoscope*, 105:494–97 (1995).
Greiling, D., and Clark, R. A. F., *J. Invest. Dermatol.*, 106:895a (1996).
Greiling, D., and Clark, R. A. F., *J. Cell Sci.*, 110:861–870 (1997).
Heldin, C. H., and Westermark, B., in "The Molecular and Cellular Biology of Wound Repair", 2d edition, Clark, R. A. F., ed, Plenum Press, New York, N.Y., pp 249–274 (1996).
Henke, C. A., et al., *J. Clin. Investigation*, 97(11):2541–2552 (1996).
Herrick, S. E., et al., *Am. J. Path.*, 141:1085–1095 (1992).
Kratz, G., et al., *Scandinavian J. of Plastic and Reconstructive Surgery and Hand Surgery*, 31(2):119–123 (June 1997).
Lamme, E. N., et al., *J. Histochemistry and Cytochemistry*, 44(11):1311–1322 (1996).
Lasa et al., *J. Surg. Res.*, 54:202–06 (1993).
Lees, T. A., and Lambert, D., *Br. J. Surg.*, 79:1032–1034 (1992).
Lindholm, C., et al., *Acta Derm Venereol (Stockh)*, 72:227–230 (1992).
McClain, S. A., et al., *Am. J. Path.*, 149:1257–1270 (1996).
Medical Data International, Inc., "Wound Card in the US: Emerging trends, management and new product development" (1993).
Mosesson, M. W., and Sherry, S., *Biochem.*, 5:2829–2835 (1966).
Nakamura, M., et al., *Experimental Eye Research*, 64(6):1043–1050 (1997).
Nanney, L. B., and King, L. E., in "The Molecular and Cellular Biology of Wound Repair", 2d edition, Clark, R. A. F., ed, Plenum Press, New York, N.Y., pp 171–194 (1996).
Ortonne, J. P., *J. Dermatological Treatment*, 7(2):75–81 (1996).
Phillips, L. G., et al., *Ann. Plast. Surg.*, 31:331–334 (1993).
Phillips, T. J., and Dover, J. S., *J. Am. Acad. Dermatol.*, 25:965–987 (1991).
Rappolee, D. A., et al., *Science*, 241:708–712 (1988).
Roberts, A. B., and Sporn, M. B., in "The Molecular and Cellular Biology of Wound Repair", 2d edition, Clark, R. A. F., ed, Plenum Press, New York, N.Y., pp 275–310 (1996).
Robson, M. C., et al., *Ann. Surg.*, 216:401–406 (1992a).
Robson, M. C., et al., *Ann. Plast. Surg.*, 29:193–201 (1992b).
Saclarides et al., *Dis. Colon Rectum*, 35:249–52 (1992).
Schultz, G., et al., *Acta Ohthalmologica*, 70(S202):60–66 (1992).
Senior, R. M., et al., *J. Cell Biol.*, 100:351–356 (1985).
Seppa, H. E. J., et al., *J. Cell Biol.*, 92:584–588 (1982).
Shaw, R. J., et al., *J. Cell Biol.*, 111:2139–2148 (1990).
Welch, M. P., et al., *J. Cell Biol.*, 110:133–145 (1990).
Xu, J., and Clark, R. A. F., *J. Cell Biol.*, 132:239–249 (1996).

Yamada, N., et al., *Scandinavian J. of Plastic and Reconstructive Surgery and Hand Surgery,* 29(3):211–219 (1995).

What is claimed:

1. A method for enhancing fibroblast migration at a wound site comprising:
    contacting the wound site with fibrinogen prepared by a process which comprises
    precipitating plasma with glycine to produce a first precipitate and a first supernatant;
    dissolving the first precipitate in a buffer to produce a first solution; and
    precipitating the first solution by adding glycine to the first solution.

2. A method according to claim 1, wherein the precipitating is carried out at temperatures below room temperature.

3. A method according to claim 1, wherein the precipitating is carried out at temperatures between about 2° C. and about 7° C.

4. A method according to claim 1, wherein the precipitating is carried out by adding glycine to plasma to produce a mixture, wherein the glycine is added in a concentration to produce glycine in the mixture of from about 1.0 to about 2.1 M.

5. A method according to claim 1, wherein the buffer has a pH of from about 6 to about 8.

6. A method according to claim 1, wherein the plasma from which fibrinogen is precipitated has a volume V and wherein the buffer has a volume of from about 0.3 V to about 0.4 V.

7. A method according to claim 1, wherein the plasma is precipitated by adding glycine to plasma to a concentration of from about 1.0 to about 2.1 M and wherein the solution is precipitated by adding glycine to the solution to a concentration of from about 1.7 to about 2.2 M.

8. A method according to claim 1, further comprising:
    dissolving a second precipitate produced by the precipitating the first solution step in a buffer to produce a second solution; and
    precipitating the second solution by adding ammonium sulfate to the second solution to produce a third precipitate and a third supernatant.

9. A method for enhancing fibroblast migration at a wound site, comprising contacting the wound site with fibrinogen prepared by a process which comprises:
    precipitating plasma with glycine to produce a first precipitate and a first supernatant and
    precipitating the first supernatant by adding glycine to the first supernatant.

10. A method according to claim 9, wherein the plasma is precipitated by adding glycine to plasma to a concentration of from about 1.0 to about 2.1 M and wherein the supernatant is precipitated by adding glycine to the supernatant to a concentration of from about 1.7 to about 2.2 M.

11. A method according to claim 9, further comprising:
    dissolving a second precipitate produced by the precipitating the first supernatant step in a buffer to produce a first solution; and
    precipitating the first solution by adding glycine to the first solution to produce a third precipitate and a third supernatant.

12. A method according to claim 11, further comprising:
    dissolving the third precipitate in a buffer to produce a second solution; and
    precipitating the second solution by adding ammonium sulfate to the second solution to produce a third precipitate and a third supernatant.

13. A method according to claim 1 further comprising:
    contacting the wound site with a growth factor, an extracellular matrix material, or mixtures thereof.

14. A method according to claim 8, wherein the third supernatant comprises a lipid rich layer.

15. A method according to claim 14, wherein the third supernatant is further treated to produce a lipid rich component.

16. A method according to claim 15, wherein the lipid rich component is separated from the third supernatant.

17. A method according to claim 12, wherein the third supernatant comprises a lipid rich layer.

18. A method according to claim 17, wherein the third supernatant is further treated to produce a lipid rich component.

* * * * *